US007148379B2

(12) United States Patent
Möller et al.

(10) Patent No.: US 7,148,379 B2
(45) Date of Patent: Dec. 12, 2006

(54) PREPARATION OF 2-HYDROXY-4-METHYLTHIOBUTYRIC ACID

(75) Inventors: Alexander Möller, Gelhausen (DE); Hans-Albrecht Hasseberg, Gründau-Lieblos (DE); Harald Heinzel, Altenstadt (DE); Volker Häfner, Langenselbold (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/212,023

(22) Filed: Aug. 25, 2005

(65) Prior Publication Data

US 2006/0047169 A1    Mar. 2, 2006

(30) Foreign Application Priority Data

Aug. 26, 2004 (DE) ............... 10 2004 041 250

(51) Int. Cl.
*C07C 323/00* (2006.01)
(52) U.S. Cl. ...................................... 562/581
(58) Field of Classification Search ............ None
See application file for complete search history.

(56) References Cited

U.S. PATENT DOCUMENTS 4,533,414 A * 8/1985 Asphahani ............ 148/427
4,912,257 A    3/1990 Hernandez et al.
5,695,716 A * 12/1997 Kohler et al. ............ 420/584.1
5,998,664 A * 12/1999 Hsu et al. ............ 562/581

FOREIGN PATENT DOCUMENTS

| EP | 0 874 811 | 7/1997 |
| EP | 0 863 135 A2 | 9/1998 |
| EP | 1 149 073 | 8/2000 |
| JP | 2003-104959 A2 | 4/2003 |
| WO | WO 96/40630 | 12/1996 |

OTHER PUBLICATIONS

Kirchheiner, R. et al., "Alloy 59, a new highly corrosion resistant material for the chemical process industry, environmental pollution control and related applications," Werkstoffe und Korrosion, Aug. 1992, pp. 388-395, vol. 43, No. 8, Verlag Chemie GmbM, Weinheim, Germany.
Köhler, M. et al., "Alloy 700 Si, a new corrosion resistant material for handling of hot, highly concentrated mineral acids," Werkstoffe und Korrosion, Jan. 1995, pp. 18-26, vol. 46, No. 1, Verlag Chemie GmbM, Weinheim, Germany.

* cited by examiner

*Primary Examiner*—Paul A. Zucker
(74) *Attorney, Agent, or Firm*—Smith, Gambrell & Russell, LLP

(57) ABSTRACT

A process for the preparation of 2-hydroxy-4-methylthiobutyric acid.

17 Claims, No Drawings

PREPARATION OF 2-HYDROXY-4-METHYLTHIOBUTYRIC ACID

The present invention relates to a process for the preparation of 2-hydroxy-4-methylthiobutyric acid, which describes the use of specific materials for the various process stages.

PRIOR ART

Nutritivity-improving feedstuffs additives are nowadays an indispensable constituent of animal nutrition. They serve for better utilization of the food supply, stimulate growth and promote the formation of protein. One of the most important of these additives is the essential amino acid methionine, which occupies a prominent position as a feedstuffs additive above all in poultry rearing. However, so-called methionine substitutes, such as methionine hydroxy analogue (abbreviated to MHA) also have a not inconsiderable importance in this field, since they have similar growth-stimulating properties to the amino acid known for this.

The racemic form of 2-hydroxy-4-methylthiobutyric acid is a methionine substitute which has been known for a long time and is chiefly used as a feedstuffs additive in animal nutrition, in particular in the rearing of poultry. This MHA can be used instead of methionine and, like this, improves the yield of breast meat on poultry. It is furthermore also used pharmaceutically in the form of its calcium salt in the treatment of renal insufficiency.

MHA is usually employed in the form of aqueous concentrates, these also comprising, in addition to the monomer, a certain content of oligomers, chiefly the di- and trimeric linear ester acids. The content of these oligomers depends on the preparation conditions and the concentration chosen.

It is generally known that 2-hydroxy-4-methylthiobutyric acid can be prepared continuously or batchwise by hydration and successive hydrolysis of 2-hydroxy-4-methylthiobutyronitrile in a sulfuric acid medium.

The synthesis is carried out, for example, in accordance with EP-A-0 874 811, but not exclusively, as follows:

The general process for the preparation of MHA starts from 3-methylthiopropionaldehyde, also called methylmercaptopropionaldehyde or MMP, which is reacted with hydrogen cyanide to give 2-hydroxy-4-methylthiobutyronitrile, also called MMP-cyanohydrin or MMP-CH (Equation I)

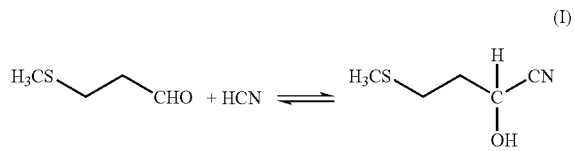

The MMP-cyanohydrin formed is then conventionally hydrolysed with strong mineral acids, such as sulfuric acid or hydrochloric acid, via the intermediate stage of 2-hydroxy-4-methylthiobutyramide, also called MHA-amide (Equation II)

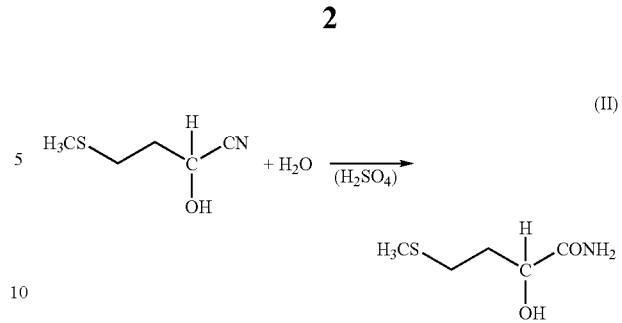

to give methionine hydroxy analogue (MHA) (Equation III).

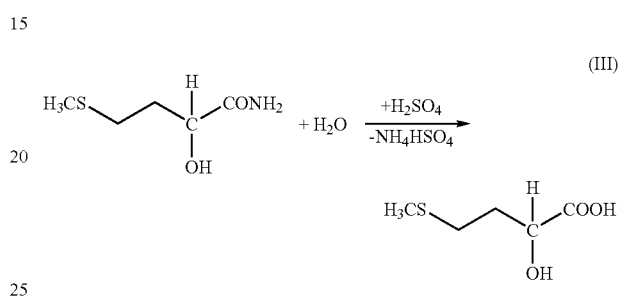

This hydrolysis can be carried out in either one or two stages, "stages" being understood as meaning that mineral acids and/or water are added either once or twice for hydrolysis of the MMP-CH.

Thus, for example, the hydrolysis of MMP-CH is carried out by a procedure in which the MMP-CH is hydrolysed in a first stage with 60–85 wt. % strength, preferably with 65–80 wt. % strength sulfuric acid in the molar ratio of MMP-CH to $H_2SO_4$ of 1.0:0.5 to 1:1.0, preferably 1:0.6 to 1:0.95, at temperatures of 30–90° C., preferably 50–70° C., for the preparation of MHA-amide. MHA-amide is formed from the MMP-cyanohydrin by this procedure, the mixture formed furthermore being substantially free from unreacted MMP-cyanohydrin. The hydrolysis proceeds virtually quantitatively. In a second stage, the MHA-amide is hydrolysed with the addition of water, without further addition of $H_2SO_4$ (a sulfuric acid concentration of <40%, for example, is established), at temperatures up to 140° C., preferably ≦110° C.

Further processes which as a rule differ only in the downstream process are moreover described. Thus, the specification JP-B-7-97970 describes the extraction of MHA from the reaction mixture with methyl isobutyl ketone. EP-A-863 135 describes another process with the addition of ammonium bisulfate to the hydrolysis solution. After the reaction, an organic solvent which is not miscible with water is added, with the result that MHA becomes concentrated in the organic phase. It is furthermore disclosed that a water-miscible organic solvent can be added to the aqueous phase in order to precipitate the corresponding ammonium sulfate.

Further processes for obtaining MHA without the use of an organic extraction solvent are described, for example, in U.S. Pat. No. 4,912,257 or EP-A-1 149 073. Various media of complex composition with various pH values and corresponding corrosiveness are present in all of these processes. This corrosiveness has the effect that considerable investment is necessary annually for maintenance as a result of incorrect choice of materials in the abovementioned process.

The apparatuses and pipelines required for production processes in corrosive complex media are conventionally manufactured from enamelled components, which are demonstrably distinguished by a high resistance to corrosion by acidic media. Enamelled components have the disadvantage that they are very sensitive to mechanical stresses such as occur in particular during assembly or the daily production operation. Once the enamelled surface has been damaged, corrosion can no longer be stopped, since the carrier material as a rule is standard steel, which is known to be not very resistant to acidic media.

A further disadvantage of enamelled components is that they must be prefabricated in a protracted manner in separate production plants and often are not available in the desired dimensions. Under certain circumstances, this can lead to long standstills of installations and resulting economic losses. Because of the poor heat transfer coefficients of enamelled components, for example, corresponding heat exchangers of large volume must be manufactured. This is likewise reflected in higher investment costs.

A further disadvantage of enamelled components is the high number of flange connections required, resulting from the limited manufacturing possibilities, which, as potential possibilities of leakage, necessitate increased expenditure on environmental protection measures. A further disadvantage of the material enamel is to be seen in the fact that because of manufacturing obstacles, the constructional degrees of freedom in the manufacture of specific resources-preserving apparatuses are severely limited.

The Patent Application WO96/40630 indeed discloses, for example, for a continuous process for the preparation of 2-hydroxy-4-methylthiobutyric acid, that corrosion-resistant materials are to be considered for the reaction apparatuses, pumps and heat exchangers employed, but there is no information as to what these materials are.

The Dechema Materials Table (1969, 1971) recommends austenitic steels for sulfuric acid media, but these are classified as non-resistant in the concentrations and temperatures required for the reaction. The stated material loss rates are not to be tolerated in respect of any resulting heavy metal impurities for the MHA end product which enters the food chain. The corrosion resistance of materials is generally determined e.g. by measurement of the material loss rates in mm p.a. as a measure of the corrosion which has taken place (definition in Römpp's Lexikon der Chemie, 1990, page 2344).

In the present connection, materials having material loss rates of at least less than 0.06 mm p.a. at temperatures of ≦60° C., or less than 0.10 mm p.a. at temperatures of ≦110° C. are to be regarded as corrosion-resistant.

It has also been reported in the Dechema Materials Table (1969) in the sulfuric acid section, sheet 17, that the corrosion resistance can be increased considerably by alloying with copper, but the material loss rates continue to be unsatisfactorily high. There is a so-called resistance gap between 31–82% strength aqueous sulfuric acid and temperatures of >20° C. for NiCrMoCu alloys. The material loss rates are, for example, approx. 0.1 mm per annum (p.a.) at 80° C. and sulfuric acid concentrations of between 10 and 78%.

It is also known from H. Zitter, Werkstoffe und Korrosion 7 (1957), 758 that steels having the composition of 18% Cr, 22% Ni, 3% Mo and 2% copper have material loss rates of up to 1.8 mm p.a. in the concentration range of 60 to 80% strength sulfuric acid at 60° C. It is furthermore known from the Dechema Materials Table that nickel alloys are corrosion-resistant in sulfuric acid media. Thus, for example, a good resistance in the concentration range of 2–96% at room temperature is stated for Hastelloy F (48% Ni, 22% Cr, 15% Fe, 6.5% Mo, 2% NS+Ta). At temperatures of 66 or 80° C., material loss rates of <8 mm p.a., which are not acceptable for the MHA process, are stated. It is furthermore reported that nickel/molybdenum/chromium alloys of the type (NiMo18Cr17W) withstand all sulfur concentrations at room temperature.

At 70° C. and sulfuric acid concentrations of <15%, the loss of material is still to be described as favourable. At higher concentrations, the peak material loss rates are up to 0.5–0.75 mm p.a. Thus, for example, according to Nickel-Informationsbüro GmbH, Düsseldorf (1961, October), page 36, the material loss rate is 0.2 mm p.a. for the alloy Hastelloy C (54% Ni, 16% Mo, 16% Cr, 4% W, 4–6% Fe, 0.05–0.07% C) at 70° C. in 40% strength sulfuric acid. Zirconium is to be regarded as the only material having acceptable corrosion rates which is suitable for the abovementioned reaction conditions, but this is prohibitive in many cases of use from the economic aspect. Standard steel having a Teflon coating or other possible materials have also been mentioned, but without being discussed in more detail. Example 22 of WO96/40630 describes the use of a flow pipe manufactured from standard steel and having a Teflon coating. Such composite construction materials have the same disadvantages as enamels, for example, but not exclusively, with respect to heat transfer coefficients and/or degrees of freedom during construction/manufacture.

OBJECT OF THE INVENTION

It is therefore the object of this invention to provide construction materials, for machines and apparatuses, which are suitable for the particular process stages of the process described above.

DESCRIPTION OF THE INVENTION

Materials which as a rule do not have the abovementioned disadvantages have now been found for the preparation of 2-hydroxy-4-methylthiobutyric acid. That is to say, superfluous flange connections can be avoided thanks to joining techniques which can be used. This reduces the susceptibility to leakages to a high degree, and contributes toward an improved protection of the environment to a large degree. Mechanical stresses such as occur in general production operation and during assembly lead to no damage which influences the corrosion properties. No limits are imposed on constructional optimization of reaction apparatuses. Thanks to the low heat transfer resistances, heat exchangers, for example, can be manufactured with a low resources-preserving construction volume.

One aspect of this invention is a process for the preparation of 2-hydroxy-4-methylthiobutyric acid, in which the addition product 2-hydroxy-4-methylthiobutyronitrile obtained by addition of hydrocyanic acid on to 3-methylthiopropionaldehyde is reacted with sulfuric acid via the intermediate 2-hydroxy-4-methylthiobutyramide, wherein the reaction of 2-hydroxy-4-methylthiobutyronitrile to give 2-hydroxy-4-methylthiobutyramide and the subsequent conversion to 2-hydroxy-4-methylthiobutyric acid are carried out in reaction containers which are corrosion-resistant for the reaction media employed and are manufactured from alloyed steel or corresponding nickel alloys.

A further aspect of the invention is a process for the preparation of 2-hydroxy-4-methylthiobutyric acid in which the addition product 2-hydroxy-4-methylthiobutyronitrile obtained by addition of hydrocyanic acid on to 3-methylthiopropionaldehyde is reacted with sulfuric acid via the intermediate 2-hydroxy-4-methylthiobutyramide, wherein the process is carried out in reaction containers of alloyed steel or corresponding nickel alloys which have a material loss rate of <0.06 mm p.a., preferably <0.025 mm p.a., particularly preferably <0.015 mm p.a., very particularly preferably <0.01 mm p.a. at temperatures of ≦60° C., and <0.1 mm p.a., preferably <0.06 mm p.a., particularly preferably <0.05 mm p.a., very particularly preferably <0.035 mm p.a. at temperatures of ≦110° C.

In contrast to the literature described above, it has been found, surprisingly, that alloys of the type, for example, XNiMoCu or NiMoCrW can be employed under the abovementioned process conditions. It has been found, surprisingly, that alloys of the type $X_1$NiMoCu, such as e.g. $X_1$NiCrMoCu 32287 (1.4562), and NiMoCrW, such as e.g. NiCr31 Mo14W (2.4602) or NiMo16Cr15W (Hastelloy C-246), have acceptable material loss rates under the conditions which prevail in the MHA process. Nevertheless, alloys of the type $X_1$NiMoCuN, for example of the type $X_1$NiMoCuN 25205 (1.4539) or $X_1$NiCrMoCu 31274 (1.4563), are not suitable. Furthermore, surprisingly, the material of the type NiCr23 Mo16Al (2.4605) or NiCr22Mo9Nb (2.4856) has proved to be suitable.

In detail, the following materials have been found for the corresponding process steps:

For the process stage of conversion of 2-hydroxy-4-methylthiobutyronitrile to 2-hydroxy-4-methylthiobutyramide, the materials 2.4602, 2.4605, 2.4856 and 1.4562 are suitable as construction materials for temperatures of ≦60° C. for reactors, heat exchangers, pumps and pipelines.

The alloys have been classified in accordance with DIN EN 10027-2 of 1992.

For the so-called hydrolysis stage of 2-hydroxy-4-methylthiobutyramide to 2-hydroxy-4-methylthiobutyric acid at temperatures of ≦110° C., only the material 2.4605 has been found to be suitable for the construction of the reactors and heat exchangers. Materials 2.4602 and 2.4605 are suitable for the pipelines. It has been found that the materials 2.4819 (Hastelloy C-276) and 2.4605 are suitable as the construction material for pumps.

The present invention is explained in more detail in the following with the aid of embodiment examples. These serve only to illustrate the invention and are in no way to be regarded as limiting in the nature and scope of this.

EXAMPLE 1

The reaction container in which 2-hydroxy-4-methylthiobutyronitrile is converted into 2-hydroxy-4-methylthiobutyramide in the presence of 65–70% strength sulfuric acid at 50–60° C. was charged with samples of material of the type 1.4562 and assessed after 250 hours. A material loss rate of <0.01 mm p.a. was determined.

EXAMPLE 2

The procedure was according to Example 1, but a sample of material of the type 2.4605 was employed. A material loss rate of <0.01 mm p.a. was determined.

EXAMPLE 3

The reaction container in which 2-hydroxy-4-methylthiobutyramide is converted to 2-hydroxy-4-methylthiobutyric acid by addition of water (sulfuric acid concentration <40%) at 110° C. was charged with samples of material of the type 2.4602 and assessed after 250 hours. A material loss rate of 0.031 mm p.a. was determined.

EXAMPLE 4

The procedure was according to Example 3, but a sample of material of the type 2.4605 was exposed to the reaction conditions for 500 hours. A material loss rate of 0.02 mm p.a. was determined.

EXAMPLE 5

The procedure was according to Example 1, but a sample of material of the type 2.4856 was employed. A material loss rate of <0.01 mm p.a. was determined.

COMPARISON EXAMPLE A

The procedure was according to Example 4, but a sample of material of the type Enamel WWG911 (supplier: Pfaudler, Pfaudler Strasse D-68723 Schwetzingen) was employed. A material loss rate of 0.021 mm p.a. was determined.

COMPARISON EXAMPLE B

The procedure was according to Comparison Example A. An Enamel 3009 (supplier: DeDietrich, Niederbronn/France) was employed. The material loss rate was 0.033 mm p.a.

COMPARISON EXAMPLE C

Reaction conditions as in Example 1 were chosen, but a material of the type 1.4539 was employed. The material loss rate was 0.069 mm p.a.

COMPARISON EXAMPLE D

The procedure was according to Example 1, but a material of the type 1.4563 was employed. A material loss rate of 0.06 mm p.a. was determined.

COMPARISON EXAMPLE E

The procedure was according to Example 3, but a material of the type 1.4562 was exposed to the reaction conditions for 250 hours. A material loss rate of 0.37 mm p.a. was determined.

The abovementioned investigations were carried out in accordance with ASTM G4-68. In these, pickled coupons (60×20 mm) of the material in question were used in the reaction medium. The pickling was carried out at room temperature for 1 to 2 hours. 24 vol % aqueous HF (40%), 8 vol % aqueous $HNO_3$ (65%) in water was used as the pickling solution.

After the test time had elapsed, the samples were washed successively with water and acetone and then dried to constant weight with a hot air fan.

The weight loss caused by corrosion was then determined by weighing and comparison with the original weight of the coupon. The material loss rate in mm p.a. was calculated from the weight loss.

A summary of all the materials investigated and their composition is given in Table 1. The results of Examples 1–5 and comparison Examples A–E are summarized in Table 2.

TABLE 1

Materials for use in the MHA process (composition data in %)

| Material no.: | Abbreviated name | Fe | Cr | Ni | Mo | Cu | Al | N | W | Nb | Mn | Co |
|---|---|---|---|---|---|---|---|---|---|---|---|---|
| 1.4539 | X1NiCrMoCuN 25 20 5 | balance | 19–21 | 24–25 | 4–5 | 1–2 | — | 0.04–0.15 | — | — | — | — |
| 1.4562 | X1NiCrMoCu 32 28 7 | balance | 26–28 | 30–32 | 6–7 | 1–1.4 | — | 0.15–0.25 | — | — | — | — |
| 1.4563 | X1NiCrMoCu 31 27 4 | balance | 26–28 | 30–32 | 3–4 | 0.8–1.5 | — | — | — | — | <=2 | — |
| 2.4602 | NiCr21Mo14W | 2–6 | 20–22.5 | balance | 12.5–14.5 | — | — | — | 2.5–3.5 | — | — | <2.5 |
| 2.4605 | NiCr23Mo16Al | max 1.5 | 22–24 | balance | 15–16.5 | — | 0.1–0.4 | — | — | — | max 0.5 | max 0.3 |
| 2.4819 | NiMo16Cr15W (Hastelloy C-276) | 4–7 | 15–16.5 | balance | 15–17 | — | — | — | 3–4.5 | — | — | <2.5 |
| 2.4856 | NiCr22Mo9Nb | 4 | 22 | balance | 9 | — | — | — | — | 3.8 | — | — |

TABLE 2

| Example/ Comparison Ex. | Material | Temperature, °C. | Duration of use (h) | Material loss rate, mm p.a. | Suitability of the material |
|---|---|---|---|---|---|
| 1 | 1.4562 | 50–60 | 250 | <0.01 | yes |
| 2 | 2.4605 | 50–60 | 250 | <0.01 | yes |
| 3 | 2.4602 | 110 | 250 | 0.031 | yes |
| 4 | 2.4605 | 110 | 500 | 0.02 | yes |
| 5 | 2.4856 | 50–60 | 250 | <0.01 | yes |
| A | Enamel WWG911 | 110 | 500 | 0.021 | yes |
| B | Enamel 3009 | 110 | 500 | 0.033 | yes |
| C | 1.4539 | 50–60 | 250 | 0.069 | no |
| D | 1.4563 | 50–60 | 250 | 0.06 | no |
| E | 1.4562 | 110 | 250 | 0.37 | no |

Further variations and modifications of the foregoing will be apparent to those skilled in the art and are intended to be encompassed by the claims appended hereto.

German priority application 10 2004 041 250.2 filed Aug. 26, 2004, is relied on and incorporated herein by reference.

The invention claimed is:

1. A process for the preparation of 2-hydroxy-4-methylthiobutyric acid, comprising reacting an addition product 2-hydroxy-4-methylthiobutyronitrile obtained by addition of hydrocyanic acid on to 3-methyithiopropionaldehyde with sulfuric acid via an intermediate 2-hydroxy-4-methylthiobutyramide, wherein the reaction of 2-hydroxy-4-methylthiobutyronitrile to give 2-hydroxy-4-methylthiobutyramide and the subsequent conversion to 2-hydroxy-4-methylthiobutyric acid are carried out in reaction containers which are corrosion-resistant for reaction media employed and are manufactured from a corrosion-resistant material which is at least one of alloyed steel and nickel alloys and wherein the corrosion-resistant materials employed have a material loss rate of <0.06 mm p.a. at temperature of 60° or of <0.1 mm p.a. at temperature of 110° C. as measured in accordance with ASTM G4-68.

2. The process according to claim 1, wherein the reaction of 2-hydroxy-4-methylthiobutyronitrile to give 2-hydroxy-4-methylthiobutyramide is carried out at temperatures of ≦60° C. in reactors, heat exchangers, pumps and pipelines which have been manufactured from a material chosen from the group consisting of 2.4602, 2.4605, 2.4856 and 1.4562.

3. The process according to claim 2, wherein the reactors, heat exchangers, pumps and pipelines have been manufactured from the material 2.4602.

4. The process according to claim 2, wherein the reactors, heat exchangers, pumps and pipelines have been manufactured from the material 2.4605.

5. The process according to claim 2, wherein the reactors, heat exchangers, pumps and pipelines are manufactured from the material 2.4856.

6. The process according to claim 2, wherein the reactors, heat exchangers, pumps and pipelines are manufactured from the material 1.4562.

7. The process according to claim 1, wherein 2-hydroxy-4-methylthio-butyramide is hydrolyzed to give 2-hydroxy-4-methylthiobutyric acid at temperatures of ≦110° C.

8. The process according to claim 2, wherein the materials employed have a material loss rate of <0.06 mm p.a. at temperature of 60° C.

9. The process according to claim 8, wherein 2-hydroxy-4-methylthiobutyramide is hydrolyzed to give 2-hydroxy-4-methylthiobutyric acid at temperatures of ≦110° C. in reactors and heat exchangers made of the material 2.4605.

10. The process according to claim 8, wherein 2-hydroxy-4-methylthiobutyramide is hydrolyzed to give 2-hydroxy-4-methylthiobutyric acid at temperatures of ≦110° C. using pipelines made of the materials 2.4602 or 2.4605.

11. The process according to claim 9, wherein the process is carried out using pipelines made of the material 2.4605.

12. The process according to claim 8, wherein 2-hydroxy-4-methylthiobutyramide is hydrolyzed to give 2-hydroxy-4-methylthiobutyric acid is carried out at temperatures of ≦110° C. using pumps made of the materials 2.4819 (Hastelloy C-276) or 2.4605.

13. The process according to claim 12, wherein the process is carried out using pumps made of the material 2.4819.

14. The process according to claim 8, wherein the materials employed have a material loss rate of <0.1 mm p.a. at temperature of 110° C.

15. The process according to claim 9, wherein the materials employed have a material loss rate of <0.1 mm p.a. at temperature of 110° C.

16. The process according to claim 10, wherein the materials employed have a material loss rate of <0.1 mm p.a. at temperature of 110° C.

17. The process according to claim 12, wherein the materials employed have a material loss rate of <0.1 mm p.a. at temperature of 110° C.

* * * * *